United States Patent [19]

Bueding

[11] 4,328,215

[45] May 4, 1982

[54] METHOD OF REDUCING OR AVOIDING THE MUTAGENIC ACTIVITY OF DRUGS

[75] Inventor: Ernest Bueding, Baltimore, Md.

[73] Assignee: The Johns Hopkins University, Baltimore, Md.

[21] Appl. No.: 795,086

[22] Filed: May 9, 1977

[51] Int. Cl.³ .................... A61K 31/71; A61K 37/00; A61K 31/625; A61K 31/47; A61K 31/415
[52] U.S. Cl. .................................. 424/181; 424/177; 424/180; 424/229; 424/258; 424/243 N; 424/302
[58] Field of Search ............... 424/302, 180, 181, 177, 424/229, 258, 273 N

[56] References Cited

U.S. PATENT DOCUMENTS 3,755,406  8/1973  Brenneisen et al. ................ 424/302

OTHER PUBLICATIONS

Bueding et al., Experientia 32, pp. 604-605, 5-15-76.
The Merck Index, 8 Ed., 1968, Merck & Co., Inc., Rahway, N.J., p. 419.

Primary Examiner—Jerome D. Goldberg
Attorney, Agent, or Firm—Cushman, Darby & Cushman

[57] ABSTRACT

A method for reducing or avoiding the transformation of a drug into a mutagenic metabolite in a host to whom the drug is administered, the method comprising administering an antibacterial agent to the host in conjunction with the administration of the drug.

9 Claims, 1 Drawing Figure

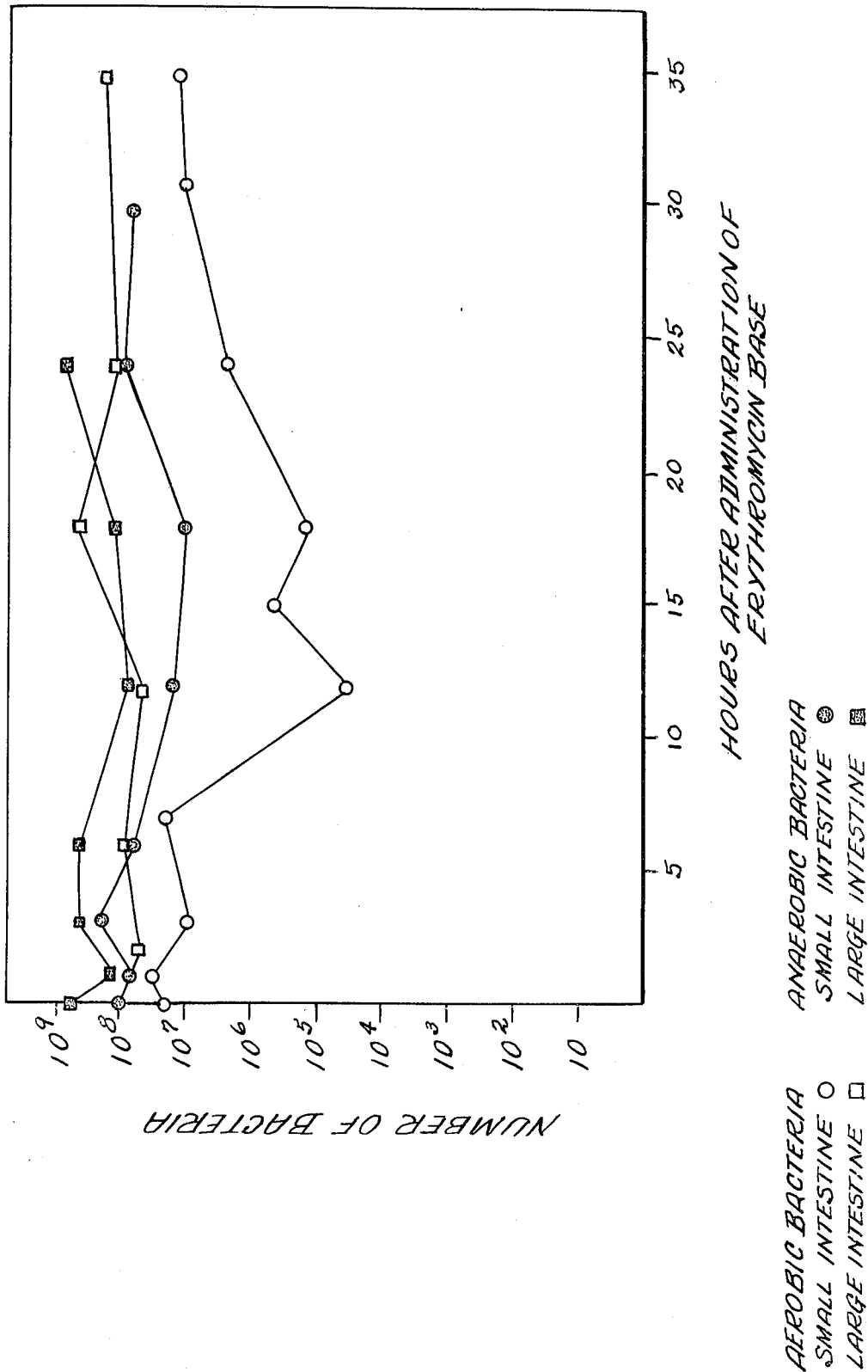

METHOD OF REDUCING OR AVOIDING THE MUTAGENIC ACTIVITY OF DRUGS

The invention described herein was made in the course of work under a grant or award from the Department of Health, Education and Welfare.

The present invention relates to a method of reducing the toxicity of compounds which have useful therapeutic and/or prophylactic properties. More particularly, the invention is concerned with a method for reducing or eliminating the mutagenic or carcinogenic activity of such compounds.

BACKGROUND OF THE INVENTION

It is well known that the usefulness of chemical compounds in the treatment and/or prevention of disease in man and other animals depends upon the chemotherapeutic ratio of such compounds, that is, the quotient of the toxic dose to the dose effective for the required purpose. As this ratio increases, the safety and consequently the usefulness of the compound increase.

Most chemical compounds which are used in the treatment or prevention of disease (hereinafter referred to for convenience as "drugs") undergo a wide range of chemical transformations in the body of the host. This is due to the action of the enzymes of the organs and tissues of the host and to the activities of extraneous biological agents present in the body of the host, principally microorganisms residing in the intestinal tract. Numerous examples can be given of drugs which themselves have low toxicity, but which are converted or metabolized by the above mentioned chemical transformations, either partially or in some cases completely, into products that demonstrate far greater chronic and acute toxic properties than the drug itself. The metabolism or transformation which occurs may or may not affect the therapeutic or prophylactic activity of the active compound. In any case, however, the transformation can reduce the chemotherapeutic ratio of the compound and, therefore, its value and scope of use. As an illustration of this, reference may be made to such antischistosomal drugs as hycanthone which, although demonstrating significant antischistosomal activity, are also mutagenic and carcinogenic apparently because of some sort of chemical transformation in the host body. As a consequence, these drugs can only find limited, if any, use since the potential benefits of using the drug need to be weighed against possible long-range risks.

OBJECTS OF THE INVENTION

The principal object of the invention is to provide a method for increasing the therapeutic ratio of drugs or like compounds. A more specific object is to provide a method whereby chemical transformations of the drug in the host body which would normally result in mutagenic or carcinogenic side effects, are substantially avoided. Another object is to provide a way of using antischistosomal drugs while avoiding the mutagenic and carcinogenic activity usually associated therewith. Other objects will also be hereinafter apparent from the following detailed description of the invention.

SUMMARY OF THE INVENTION

The invention is based on the finding that mutagenic and carcinogenic activity demonstrated by drugs, particularly antischistosomal drugs, can be minimized or substantially completely eliminated while retaining effective drug activity, by co-administering one or more antibacterial agents with the drug. It is noted, in this connection, that the transformation of drugs into undesired toxic metabolites is apparently due, at least in part, to the presence of constituents of the microbial flora in the host, notably in the gastrointestinal tract. The host tissues may also play a role in the formation of the mutagenic metabolite. In any case, use of the antibacterial agent as proposed herein appears to modify or eliminate the constituents of the microbial flora of the host that are responsible for transforming the drug into mutagenic or carcinogenic metabolites so that these metabolites are not formed. As a consequence, the drug can be effectively used for its therapeutic/prophylactic function without the undesired mutagenic and carcinogenic side effects which are normally encountered.

DETAILED DESCRIPTION OF THE INVENTION

The antibacterial agent used in the practice of the invention should be selected on the basis of the drug being used and the toxic metabolite which would otherwise be formed thereby in the body of the host. In this connection, it will be appreciated that the specific metabolic activity can be the consequence of the action of only a small segment of the microbial population of the intestinal tract. Consequently, elimination of the undesired metabolic activity is possible by the highly selective elimination of a specific fraction of the microbial population of the intestinal tract, which might not involve a substantial reduction in the total number of organisms. In other words, the invention contemplates the selective elimination of the offending component of the gastrointestinal flora by suitable choice of antibacterial agents that are specifically selected for this purpose taking into account the drug used, the metabolite which is formed and the microbial flora involved in the formation of the metabolite. The antibacterial agent selected for use with any particular drug, in the event the metabolite and the flora involved are not already known, can be readily determined on the basis of straightforward art-recognized tests as noted below for determining mutagenic activity.

The antibacterial agent or mixture of agents can be administered prior to, or simultaneously with, the drug. Preferably the antibacterial administration is carried out orally since this is the most effective way of introducing the agent into the intestinal tract to modify or eliminate the microbial flora therein. The drug involved can be administered in conventional manner, form and dosage, e.g. orally or parenterally.

The amount of antibacterial agent selected for use in any particular situation will vary depending on the agent and drug involved. This can be readily determined by use of the "Ames" test (identified more fully below) which provides, by urine analysis, a straightforward way of determining whether or not a particular drug is mutagenic. Thus, if the Ames test shows that a drug when used alone is mutagenic, it is a simple matter to recheck the results when a selected antibacterial agent is co-administered with the drug. Normally the amount of antibacterial agent used will be in the range of 5 to 50 mg/kg body weight although amounts outside this range may also be used.

It appears that any antibacterial agent which is safe and effective against the intestinal bacterial flora can be used for present purposes. Typically such agents include conventional antibiotics of the penicillin and tetracycline families as well as erythromycin base, erythromycylamine, bacitracin and succinyl sulfathiazole. Erythromycin is particularly useful because it appears to be the least toxic of the available antibiotics and does not readily produce resistant bacterial strains.

The invention is applicable to any drug in which the therapeutic/prophylactic activity is dissociated from any mutagenic or carcinogenic activity resulting from transformation or modification of the drug in the host by the intestinal microbial flora. Many antiparasitic drugs including schistosomicides are mutagenic or carcinogenic. However, some of them retain their chemotherapeutic activity when the invention is used with them. Typical examples of antiparasitic agents which may be used according to the invention are the antiprotozoal drug metronidazole and the schistosomicides oxamniquine and 4-nitro-4'-isocyanatodiphenylamine (identified herein as CGP 4540), the latter being described in U.S. Pat. No. 3,755,406.

The invention is illustrated below using standard test techniques for determining mutagenic activity of drugs. In this connection, it should be noted that most known carcinogenic compounds exhibit mutagenic effects on certain strains of *Salmonella typhimurium.* Conversely, few compounds found to be noncarcinogenic exhibit mutagenic activity. Because of this close correlation, the results of mutagenic assays provide a high degree of probability in predicting carcinogenic activity. While bacteria lack many enzymes catalyzing the metabolism of drugs in mammals, carcinogenic and mutagenic metabolites can be detected in several ways, namely, (1) by adding liver microsomes in vitro to the bacteria incubated with the test substance (Ames et al., Proc. Nat. Acad. Sci., U.S.A. 70: 2281–2285, 1973); (2) by host mediated assays involving the incubation of bacteria in the peritoneal cavity of animals to which the test substance has been administered (Legator et al, Chemical Mutagens, Principles and Methods for Their Detection, ed. by A. Hollaender, Vol. 2, pages 569–589, 1971); or (3) by determination of the mutagenic activity of the urine of these animals (Durston and Ames, Proc. Nat. Acad. Sci. U.S.A. 71: 737–741, 1974).

In the present case, methods (2) and (3) have been used to determine mutagenic and presumably carcenogenic activity of the drugs tested. While specific details for these test methods may be varied, the following can be given as representative:

Host-mediated assays. Overnight bacterial cultures are diluted 4-fold with 2X nutrient broth and reincubated at 37° C. for 2 hours. Two hours prior to administration of the bacteria, drugs are administered by gastric intubation. The selected number of 6- to 8-week-old female mice (mixed Swiss-Webster, CF-1, Charles River) are used for each dose level. Two milliliters of the culture are injected intraperitoneally. After 6 hours the bacteria are retrieved from the peritoneal cavity by the injection and removal of 2 ml of 0.85% NaCl. These exudates are plated to determine the number of revertants and a 1:10$^6$ serial dilution is plated with 0.2 ml of added nutrient broth to determine the number of viable bacteria. Plates are counted after 48 hours of incubation at 37° C. and results are expressed in terms of revertants per million bacteria.

Urine analysis (referred to above as the "Ames" test). Mice are placed into a metabolism cage and control urines are collected on ice for 24 hours. These animals are then treated with the drug and urine is collected in refrigerated containers for the two subsequent 24-hour periods. The volume of the urine is measured and the urine is stored at −80° C. until assayed.

Urine specimens are thawed, centrifuged at 10,000×g for 15 minutes and sterilized by filtration through a 0.22 μm Millipore filter. Effects of 0.1 and 0.25 ml aliquots are tested on strains TA 100 with and without added S9 microsomal fraction. Plates are counted after incubation at 37° C. for 48 hours. The dose response at these two urine concentrations is used to calculate the number of revertants induced by the total volume of urine excreted in 24 hours. In order to determine whether some mutagens are present as inactive urinary glucuronate or sulfate conjugates, aliquots of the mouse urines are incubated for 3 hours at 37° C. and pH 4 with β-glucuronidase (12.5 mU/ml of urine)-arylsulfatase (6.25 mU/ml of urine) (Boehringer). Aliquots of this mixture are tested after adjustment to pH 7 in the absence and the presence of the S9 fraction.

The following examples are given for the purpose of illustrating the invention:

EXAMPLE 1

The schistosomicide 4-nitro-4'-isocyano diphenylamine (CGP 4540) was orally administered to two germ-free rats and two conventional male Fisher rats weighing 220–240 grams. Urines from the thus treated animals were analyzed for mutagenic activity and assays were carried out as described in Journal of Pharmacology and Experimental Therapeutics, 200, 1–9 (1977) using the methodology of Ames et al (*Mutat. Res.,* 31, 347–364). The mutagenic activities of the urines were determined in both the absence and presence of S$_9$ (hepatic microsomal) fractions of phenobarbital pretreated rats (Ames et al, *Proc. Nat. Acad. Sci,* U.S.A., 71, 737–741, 1974) without and with preincubation with β-glucuronidase.

For test purposes, the isothiocyanate derivative was dissolved at 40° C. in a polyethoxylated vegetable oil (Emulphor El 620) to a final concentration of 50 mg/ml. Following sterilization by means of millipore filtration the mixture was administered by gastric intubation to two germ-free and two conventional male Fisher rats (weighing 220 to 240 gms) at a dose of 250 mg/kg of the isothiocyanate. One germ-free and one conventional rat that were given the filtered vehicle without the drug served as controls. The urines of each animal were collected for a period of 48 hours subsequent to administration of the drug or the filtered vehicle.

The germ-free rats used in the tests were kept in Tresder type plastic isolators. After administration of the isothiocyanate or the vehicle the germ-free rats were transferred into individual metabolism cages in the isolators.

The mutagenic activity determined for the test animals, expressed in terms of revertants in excess of the controls, is shown below:

TABLE I

| | | Revertants in excess of controls excreted in 24 hrs | | | |
|---|---|---|---|---|---|
| | | 0–24 hrs | | 24–48 hrs | |
| Rat # | Type | −S$_9$ | +S$_9$ | −S$_9$ | +S$_9$ |
| 1 | Germ-free | 0 | 0 | 0 | 0 |
| 2 | | 0 | 0 | 0 | 0 |
| 3 | Conventional | 3,800 | 4,900 | 1,600 | 2,800 |
| 4 | | 3,750 | 5,000 | 1,200 | 3,050 |

As will be evident, the urines of the germ-free rats (1) and (2) showed no difference in revertants or mutagenic activity over the controls, i.e. no mutagenic metabolite was detectable in these urines. On the other hand, the mutagenic activity in the urine of conventional rats was substantially increased both in the absence ($-S_9$) and in the presence ($+S_9$) of a liver microsome fraction. The greater increase demonstrated in the presence of the liver microsome fraction indicates that the urines involved contained material which was mutagenic following metabolic activation. No further increase in mutagenic activity was observed after incubation (for 3 hrs at 37° C.) of the urines with $\beta$-glucuronidase.

EXAMPLE 2

This example illustrates the effects of coadministered erythromycin base and erythromycylamine on the mutagenic activity in vivo of formulated CGP 4540 administered orally to mice. The mice were infected with *S. typhimurium* TA 100 as the test strain and the CGP 4540 was formulated as in Example 1. The CGP 4540 was administered orally to the mice at a dosage of 250 mg/kg (estimated at about 25 times the curative dose) following a single orally administered dose (100 mg/kg) of either erythromycin base or erythromycylamine. Three control mice were employed. Erythromycin was orally administered to one of the control mice at a dosage of 100 mg/kg and erythromycylamine was similarly administered to another control. None of the control animals received any CGP 4540 although they were given an equal amount of vehicle as in Example 1. The mutagenic activity of urines from the various test animals was measured by determining the number of revertants therein in excess of the controls per total 24 hour urine excreted per mouse. Host mediated assays were also performed to determine the number of revertants per $10^8$ bacteria. The results were as follows:

As will be evident from Table II, following coadministration of a single oral dose of erythromycin base or of erythromycylamine with 25 times the curative schistosomicidal dose of formulated CGP 4540, no mutagenic activity was detectable either in the host mediated assay or in the urines.

EXAMPLE 3

This example shows that coadministration of the antibacterials of Example 2 does not reduce the curative antischistosomal activity of CGP 4540. Six groups of test mice, infected with *Schistosoma mansoni*, were treated as follows:

(1) a single dose of formulated CGP 4540 (10 mg/kg) with no antibiotic administered;
(2) single dose of formulated CGP 4540 as in (1) but preceded by 100 mg/kg of erythromycin (base);
(3) same as (2) but using erythromycylamine as the antibiotic;
(4) same as (1) but using a CGP 4540 dosage of 15 mg/kg;
(5) same as (4) but preceded by a 100 mg/kg dose of erythromycin; and
(6) same as (5) but using erythromycylamine as the antibiotic.

All drugs were administered by gastric intubation. The following results were obtained:

TABLE III

Antischistosomal activity of formulated CGP4540 in mice infected with *Schistosoma mansoni* and treated with two antibiotics.

| Single dose of formulated CGP 4540 mg/kg | Coadministered antibiotic (100 mg/kg) | No. of mice | Reduction in number of worms % | Mice with parasitological cures % |
|---|---|---|---|---|
| 10 | None | 196 | 99 | 96 |
| | Erythromycin (base) | 18 | 100 | 100 |
| | Erythromycylamine | 17 | 100 | 100 |
| 15 | None | 16 | 100 | 100 |
| | Erythromycin (base) | 18 | 100 | 100 |
| | Erythromycylamine | 19 | 100 | 100 |

The results of Table III show that the curative antischistosomal activity of CGP 4540 is not reduced by the preceding treatment with either of the indicated antibiotics.

The Examples 1-3 indicate that pretreatment of the host with antibacterial agent makes it possible to prevent production of a mutagenic metabolite while maintaining the desired antiparasitic activity of the schistosomicidal compound. In other words, in this instance, mutagenic and chemotherapeutic activities can be disso-

TABLE II

Effects of coadministered erythromycin base and of erythromycylamine (100 mg/kg orally) on the mutagenic activity in vivo of formulated CGP 4540 (250 mg/kg) administered orally to mice - Tester strain: *S. typhimurium* TA100

| | Host mediated assay Revertants per $10^8$ bacteria | | | Mutagenic activity of urines. Number of revertants in excess of controls per total 24 hour urine excreted per mouse | | | |
|---|---|---|---|---|---|---|---|
| | | | | Day 1 | | Day 2 | |
| Coadministered | Controls (No CGP4540) | 250 mg/kg CGP4540 | Revertants in excess of controls | No S9 | +S9 | No S9 | +S9 |
| None | 68 (±2) | 172 (±9) | 104 | 120 | 541 | 32 | 89 |
| Erythromycin | 65 (±4) | 66 (±3) | 1 | 0 | 0 | 0 | 0 |
| Erythromycylamine | 65 (±4) | 64 (±1) | 1 | 0 | 0 | 0 | 0 | ciated completely from each other. This is an important aspect of the invention since it makes it possible to obtain the desired advantages of the drug without its undesired mutagenic or carcinogenic effects. In this sense, the mutagenic activation of the antischistosomal isothiocyanate appears to be analogous to that of cycasin. The conversion of this glycoside to methylazoxymethanol, a mutagen and carcinogen, is catalyzed by a $\beta$-glucosidase of intestinal bacteria. (Smith, D. W. E. (1966). *Science* (Washington) 152, 1273–1274 and Spatz, M., Smith, D. W. E. McDaniel, E. G. and Laqueur, G. L. (1967). *Proc. Soc. Exp. Biol. Med.*, 124, 691–699.) Furthermore, the formation of the aglycone is prevented by the administration of an antibacterial agent, i.e., ampicillin, and does not occur in germ-free animals.

An essentially equivalent effect is obtained when the antibacterial agent is succinylsulfathiazole. Thus, it has been found that the oral administration of succinylsulfathiazole (1 g/kg once daily for 3 successive days) to mice, preceding the administration of formulated CGP 4540, essentially on the lines of Example 2, reduces the bacterial flora of the host's intestines and gives a very marked decrease in the mutagenic urinary metabolite, and of the mutant colonies found in the host-mediated assay. This reduction of the bacterial flora and accompanying decrease in mutagenic activity do not appear to affect the antischistosomal activity of the CGP 4540.

While Examples 1-3 refer specifically to the schistosomicidal CGP 4540, similar tests using the antiprotozoal drug metronidazole, which is also normally mutagenic and carcinogenic, show that the mutagenic activity of this compound in vivo can be reduced by pretreatment of the host with similar antibacterial agents. Additionally, it has been found that the antibacterial agents are synergistic with antioxidants in reducing markedly (to the extent of over 90%) the mutagenic effect of metronidazole. This is demonstrated by the following:

EXAMPLE 4

The two mutagenic tester strains TA 100 and TA 98 were injected into the intraperitonal cavity of conventional mice to which a single does of 400 mg/kg of metronidazole had been administered orally. Control mice (1) received only the metronidazole while another group (2) of mice also received butylated hydroxyanisole (BHA) in its diet (0.75% by weight BHA); a third group (3) was given a mixture of antibacterial agents, specifically a single oral dosage of succinylsulfathiazole (1 gm/kg), erythromycin base (200 mg/kg) and bacitracin (200 mg/kg) just prior to the administration of the metronidazole; and a fourth group (4) was given both BHA in the diet as in (2) and a pretreatment with the antibacterial mixture as in (3).

After six hours, the tester strains were withdrawn from the peritoneal cavity of all the mice and placed on a conventional agar medium according to the Ames method and the number of revertants obtained in excess of controls per $10^8$ bacteria determined. The following results were obtained:

TABLE IV

| Mice Additional Treatment | Revertants in excess of controls per $10^8$ bacteria | |
|---|---|---|
| | TA100 | TA98 |
| (1) None - control | 771 | 176 |
| (2) BHA diet | 144 } 141 138 | 100 |
| (3) Antibacterial agents | 304 | 35 |
| (4) BHA diet and Antibacterial agents | 65 } 65 65 | 9 |

It will be evident that the combination of BHA and antibacterial agents reduced the number of revertants by more than 90% in the case of both TA 100 and TA 98. It is also evident that use of the antioxidant BHA without the antibacterial agent serves to substantially reduce the mutagenic activity of metronidazole. A similar effect has been observed with other mutagenic and carcinogenic compounds such as benz(a)pyrene, hycanthone, other polycyclic aromatic hydrocarbons and acetylamino-fluorene.

The unique results of the invention have also been demonstrated with oxamniquine, another antischistosomal drug which is used widely in the treatment of human schistosomiasis in Brazil and other parts of the Western hemisphere where this infection is prevalent. It also is used, though to a lesser extent, in Africa and the Mid-east for the treatment of *schistosomiasis mansoni*. When administered to mice and monkeys, it has been found that this drug gives rise to the appearance of a mutagenic metabolite in the urine of these animals (see "Mutagenic Activities In Vitro and In Vivo of Five Antischistosomal Compounds" by Batzinger and Bueding, *The Journal of Pharmacology and Experimental Therapeutics*, Vol. 200, No. 1 (1977)). Nevertheless, it has been found that co-administration of antibacterial agents (a mixture of erythromycin, bacitracin and succinyl sulfathiazole as above) with oxamniquine according to the present invention completely eliminates the appearance of the mutagenic metabolite.

A further advantage of the invention is that, at least in some instances, acute hepatotoxic effects resulting from use of an antischistosomal or other drug and caused by a metabolic product, may be prevented. Thus, for example, at very high doses of the antischistosomal isothiocyanate (CGP 4540), i.e., at 50 times the curative dose or 500 mg/kg, some destructive lesions may be produced in the bile ducts and the liver. However, these lesions are prevented by the co-administration of an antibacterial agent, such as erythromycin according to the invention. Accordingly, in this particular situation the administration of the antibacterial agent not only prevents the mutagenic effects of a metabolic product of the intestinal bacterial flora but also the acute hepatotoxic effects which might otherwise be encountered.

Example 5

The advantage of using one or more antibacterial agents as a pretreatment before the administration of CGP 4540 according to the invention, in reducing mutagenic activity, is further shown by the tables set forth hereinafter:

TABLE V

Mutagenic Activity of Formulated CGP 4540 Administered Orally to Mice

| Pretreatment | Controls (no CGP 4540) | CGP 4540 (250 mg/kg) | Revertants in excess of controls |
|---|---|---|---|
| None | 68(±2) | 172(±9) | 104 |
| Succinylsulfathiazole (1 g/kg) | 62(±5) | 106(±3) | 44 |
| Bacitracin (220 mg/kg) | 64(±9) | 127(±11) | 63 |
| Succinylsulfathiazole (1 g/kg) + bacitracin (220 mg/kg) | 73(±4) | 71(±2) | 0 |
| Bacitracin (440 mg/kg) | 71(±5) | 72(±6) | 0 |
| Bacitracin (220 mg/kg) + neomycin (7.5 mg/kg) | 73(±6) | 69(±6) | 0 |

Activity was determined by means of a host-mediated assay of *Salmonella typhimurium* strain TA 100. Figures indicate number of revertants per $10^8$ bacteria with standard error of the mean given in parentheses.

TABLE VI

Mutagenic Activity of the Urines of Mice Treated with Formulated CGP 4540 on *Salmonella typhimurium* Strain TA 100 in the Absence and Presence of Rat Liver Microsome Fraction ($S_9$)

| Pretreatment or coadministration (oral) | Oral dose CGP 4540 (mg/kg) | No. of revertants in excess of controls* | | | |
|---|---|---|---|---|---|
| | | day 1 | | day 2 | |
| | | no $S_9$ | $+S_9$ | no $S_9$ | $+S_9$ |
| None | 100 | 56 | 239 | 11 | 30 |
| | 250 | 120 | 541 | 32 | 89 |
| Succinylsulfathiazole (1 g/kg) | 100 | 37 | 108 | 0 | 12 |
| | 250 | 73 | 269 | 7 | 30 |

TABLE VI-continued

Mutagenic Activity of the Urines of Mice Treated with Formulated CGP 4540 on *Salmonella typhimurium* Strain TA 100 in the Absence and Presence of Rat Liver Microsome Fraction ($S_9$)

| Pretreatment or coadministration (oral) | Oral dose CGP 4540 (mg/kg) | No. of revertants in excess of controls* | | | |
|---|---|---|---|---|---|
| | | day 1 | | day 2 | |
| | | no $S_9$ | $+S_9$ | no $S_9$ | $+S_9$ |
| Bacitracin (220 mg/kg) | 250 | 31 | 96 | 4 | 10 |
| Succinylsulfathiazole (1 g/kg) + bacitracin (220 mg/kg) | 250 | 0 | 0 | 0 | 0 |
| Bacitracin (440 mg/kg) | 250 | 0 | 0 | 0 | 0 |

*Per total 24-hour urine excreted per mouse.

It is to be noted that when the intestinal bacterial flora was reduced by coadministration of antibacterial agents, the mutagenic activities in the host-mediated assay either decreased of disappeared (Table V). Furthermore, the decrease in mutant colonies produced by the coadministration of the isothiocyanate with succinylsulfathiazole or bacitracin was paralleled by a reduction in the urinary mutagenic metabolite, and when the host-mediated assay was negative after coadministration with succinylsulfathiazole plus bacitracin, or with a higher dose of bacitracin alone, the urinary mutagenic metabolite was no longer detectable (Table VI). Therefore a mutagenic metabolite of the antischistosomal isothiocyanate is produced by the intestinal bacterial flora, rather than by the tissues of the host, and intestinal antibacterial agents can eliminate its formation.

As noted earlier, the antibacterial treatment does not alter the high schistosomicidal activity of a single low dose of the isothiocyanate derivative. Single low doses of the drug formulation are nearly or equally as effective whether or not the antibacterial agents are administered as shown in the following table:

TABLE VII

Chemotherapeutic Activity of Formulated CGP 4540 in Mice Infected with *Schistosoma mansoni* and Treated with Antibacterial Drugs

| Single dose CGP (mg/kg) | Antibacterial treatment | No. of mice | Reduction in no. of worms (%) | Mice with parasitological cures (%) |
|---|---|---|---|---|
| 10 | None | 196 | 99 | 95 |
| | Bacitracin (440 mg/kg) | 45 | 98 | 88 |
| | Succinylsulfathiazole(1 g/kg) + bacitracin (220 mg/kg) | 53 | 99 | 92 |
| 20 | None | 141 | 100 | 100 |
| | Bacitracin (440 mg/kg) | 47 | 100 | 100 |
| | Succinylsulfathiazole(1 g/kg) + bacitracin (220 mg/kg) | 42 | 100 | 100 |

All drugs were administered by gastric intubation.

It is thus clear that schistosomicidal and mutagenic activities can be dissociated completely from each other, demonstrating that the mechanisms bringing about schistosomicidal effects are different from those responsible for mutagenic properties of a given compound.

The available evidence indicates that the transformation of CGP 4540 and other antischistosomal drugs to give mutagenic and carcinogenic effects occurs in the intestinal tract, either in the intestinal mucosa or in association with the intestinal flora. This is evident, for example, from the fact that, while both oral and intramuscular administration of formulated CGP 4540 are about equally effective against schistosomiasis, the conversion of CGP 4540 to a mutagenic metabolite is 50% greater when given orally than when injected intramuscularly or intravenously. This also indicates that there might not be an obligatory association between the therapeutic and mutagenic activities of the drug.

It is also evident that the lack of mutagenic activity of the urines excreted by the germ-free rats is not caused by material interfering with the bacterial test system. This is shown by the fact that, after addition of the mutagenic metabolite to the urines of the germ-free rats, all the mutagenic activity was recovered in this mixture as shown below.

TABLE VIII

The mutagenic activity of urinary mutagenic metabolite of CGP4540 in the presence and absence of urine from germ-free rats treated with 250 mg/kg formulated CGP4540 assayed with tester strain TA100 with and without added phenobarbital-induced rat liver microsomes ($S_9$).

| | Revertants in excess of controls | |
|---|---|---|
| | $-S_9$ | $+S_9$ |
| Urinary metabolite (0.1 μmole) | 71 | 166 |
| .25 ml germ-free rat urine | 0 | 0 |
| .1 μmole isolated metabolite + .25 ml germ-free rat urine | 72 | 160 |

The mutagenic metabolite of CGP 4540 used in the test described immediately above was isolated from urines of hamsters that had received the formulated isothiocyanate by gastric intubation at a dose level of 250 mg/kg of body weight. After extraction of the urine (saturated with NaCl) with one volume of butanol, one volume of n-heptane was added to the organic phase and the metabolite was extracted from this mixture with 0.1 volume of water. After evaporation of the aqueous phase the residue was chromatographed over a silica column with 20% ethylacetate-80% butanol and the eluted mutagenic material was fractionated further using another silica column with 5% ethylacetate in butanol as the eluent.

When extracts of the urines of conventional rats treated with the isothiocyanate were collected 0 to 24 hours after oral administration of 250 mg/kg of the formulated CGP 4540 and chromatographed on a thin layer silica plate using a solvent mixture of 95% butanol and 5% ethylacetate, a spot with an $R_f$ similar to that of the isolated mutagenic metabolite was recognizable. No such spot appeared in the chromatogram of the urine extract of germ-free rats.

EXAMPLE 6

In order to determine the overall effect of the antibiotic used in Example 3 on intestinal bacteria, a single dose of erythromycin base was orally administered to mice (100 mg/kg) and the number of aerobic bacteria in the large and small intestines of the mice was determined at various time intervals following administration of the antibiotic. Homogenates of these organs were made with 10 ml nutrient broth (Difco) and serial dilutions were plated on nutrient agar plates. Obligatory anaerobic bacteria were counted in the same manner except that the organs were homogenized in thioglycolate (Difco) medium and the agar plates were incubated in anaerobic jars. The plates were counted after incubation for 24 hours at 37° C. There were no significant differences in counts when the incubation time was extended for 48 hours. Six mice were used for each time interval.

The results are shown in FIG. 1 wherein the number of aerobic bacteria in the small and large intestines are shown, respectively, by open circles and open squares while the number of anaerobic bacteria are shown in the small and large intestines by the closed circles and squares, respectively. As will be evident, with the single dose of erythromycin, which was effective to eliminate the mutagenic activity of CPG 4540 (Example 3), there was only a moderate reduction, of relatively short duration, in the total number of aerobic bacteria in the small intestine and little, if any, change in the large intestine in the number of aerobes and anaerobes. In the small intestine, anaerobic bacteria were reduced to an even lesser extent than were aerobes.

The examples given above demonstrate that the mutagenic risks of the antischistosomal isothiocyanate (CGP 4540), metronidazole and oxamniquine are eliminated, or at least very substantially reduced, by coadministration of these drugs with certain antibacterial agents, particularly erythromycin, bacitracin and succinylsulfathiazole. However, the invention should not be considered as limited to the indicated antiparasitic drugs. Thus, as noted earlier, the invention is considered to be applicable to any therapeutic or prophylactic agent which is converted to a mutagenic metabolite where such metabolite is not significantly associated with the therapeutic or propylactic activity of the drug.

Accordingly, the scope of the invention is defined by the following claims wherein I claim:

1. A method for reducing or avoiding the formation of a mutagenic metabolite from a drug which is transformed into a mutagenic metabolite by intestinal bacterial flora in man or other animal to whom said drug is administered in therapeutically effective amount, and whose therapeutic or prophylactic activity is dissociated from any mutagenic activity thereof, said method comprising orally administering an antibacterial agent, which is effective against said intestinal bacterial flora, to said man or animal in conjunction with the administration of said drug, the amount of antibacterial agent so administered being sufficient to reduce said flora and thereby avoid or reduce the formation of said mutagenic metabolite from said drug by said flora and being within the range of 5 mg to 50 mg per kg body weight of said man or other animal.

2. The method of claim 1 wherein said antibacterial agent is orally administered as a pretreatment before the administration of said drug.

3. The method of claim 2 wherein the antioxidant butylated hydroxyanisole is also administered with the antibacterial agent.

4. The method of claim 1 wherein the antibacterial agent is selected from the group consisting of erythromycin base, erythromycylamine, succinylsulfathiazole and bacitracin.

5. The method of claim 1 wherein the drug is the schistosomicide 4-nitro-4'-isocyano diphenylamine and the antibacterial agent is erythromycin.

6. The method of claim 1 wherein the drug is selected from the group consisting of 4-nitro-4'-isocyano diphenylamine, oxamniquine and metronidazole.

7. A pharmaceutical composition in orally administrable form comprising a pharmaceutically effective amount of a drug which is transformed into a mutagenic metabolite by intestinal bacterial flora in man or other animal to whom said drug is administered in therapeutically effective amount, and whose therapeutic or prophylactic activity is dissociated from any mutagenic activity thereof, and an antibacterial agent which is effective against said intestinal bacterial flora, said antibacterial agent being present in an amount sufficient to reduce said flora and thereby avoid or reduce the formation of said mutagenic metabolite from said drug by said flora, the amount of said agent being within the range of 5 mg to 50 mg per kg body weight of said man or animal.

8. A composition according to claim 7 wherein the drug is 4-nitro-4'-isocyano diphenylamine, oxamniquine or metronidazole.

9. A composition according to claim 7 wherein the antibacterial agent is selected from the group consisting of erythromycin base, erythromycylamine, succinylsulfathiazole and bacitracin.

* * * * *